(12) United States Patent
Chan

(10) Patent No.: US 8,550,295 B2
(45) Date of Patent: Oct. 8, 2013

(54) CONTAINER FOR DISPENSING A SINGLE TEST STRIP

(75) Inventor: Frank A. Chan, Sunnyvale, CA (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 490 days.

(21) Appl. No.: 12/709,889

(22) Filed: Feb. 22, 2010

(65) Prior Publication Data
US 2011/0204079 A1  Aug. 25, 2011

(51) Int. Cl.
*G07F 11/16* (2006.01)

(52) U.S. Cl.
USPC .......................................... 221/232; 221/256

(58) Field of Classification Search
USPC ........... 221/25, 69, 75, 87, 89, 208, 209, 246, 221/263, 268
See application file for complete search history.

(56) References Cited

U.S. PATENT DOCUMENTS

| | | | |
|---|---|---|---|
| 2,072,796 A * | 3/1937 | Christopher | 221/260 |
| 3,115,991 A | 12/1963 | Carew et al. | |
| 5,282,950 A | 2/1994 | Dietze et al. | |
| 5,395,504 A | 3/1995 | Saurer et al. | |
| 5,407,554 A | 4/1995 | Saurer | |
| 5,525,297 A | 6/1996 | Dinger et al. | |
| 5,660,791 A | 8/1997 | Brenneman et al. | |
| 5,797,693 A | 8/1998 | Jaeger | |
| 5,810,199 A | 9/1998 | Charlton et al. | |
| 5,872,713 A | 2/1999 | Douglas et al. | |
| 6,491,186 B1 | 12/2002 | Wiggins | |
| 6,508,380 B1 | 1/2003 | von Schuckmann | |
| 6,534,017 B1 | 3/2003 | Bottwein et al. | |
| 6,827,899 B2 | 12/2004 | Maisey et al. | |
| 6,872,358 B2 | 3/2005 | Hagen et al. | |
| 6,908,008 B2 | 6/2005 | Pugh | |

(Continued)

FOREIGN PATENT DOCUMENTS

| | | |
|---|---|---|
| DE | 2 652 370 | 5/1978 |
| DE | 296 20 368 U1 | 3/1997 |

(Continued)

OTHER PUBLICATIONS

European Patent Application No. 1101276 Extended Search Report and Search Opinion mailed Oct. 14, 2011.

(Continued)

*Primary Examiner* — Gene Crawford
*Assistant Examiner* — Kelvin L Randall, Jr.
(74) *Attorney, Agent, or Firm* — Woodard, Emhardt, Moriarty, McNett & Henry LLP

(57) ABSTRACT

The test strip containers accurately dispense one test strip for easy removal. One test strip container includes a slider with a slot that catches a single test strip therein from a stack positioned inside the container. The slider retaining the single test strip moves across the container while the single test strip rides along a ramp or track on the exterior of the container until the single test strip extends above the container. Another test strip container includes inner and outer cylinders. The inner cylinder defines an opening through which a test strip from a stack is dispensed and an external ramp or track. As the outer cylinder rotates about the inner cylinder, a recessed slot in the outer cylinder captures a single test strip, and continued rotation of the outer cylinder causes the test strip to ride along the ramp or track to extend above the cylinders for removal.

10 Claims, 6 Drawing Sheets

(56) References Cited

U.S. PATENT DOCUMENTS

| | | |
|---|---|---|
| D510,711 S | 10/2005 | Syme et al. |
| 6,997,343 B2 | 2/2006 | May et al. |
| 7,063,234 B2 | 6/2006 | Giraud |
| 7,240,565 B2 | 7/2007 | Eisenmann et al. |
| 7,246,720 B1 | 7/2007 | Montoya, Jr. |
| 7,337,918 B2 | 3/2008 | Fowler et al. |
| 7,449,148 B2 | 11/2008 | Matsumoto et al. |
| 7,455,451 B2 | 11/2008 | Pearl et al. |
| 7,552,843 B2 | 6/2009 | Kuriger et al. |
| 2003/0186445 A1 | 10/2003 | Pugh |
| 2003/0186446 A1* | 10/2003 | Pugh ................................ 436/46 |
| 2006/0182656 A1 | 8/2006 | Funke et al. |
| 2007/0264165 A1 | 11/2007 | Chan et al. |
| 2008/0094804 A1* | 4/2008 | Reynolds et al. ............. 361/727 |
| 2008/0299009 A1 | 12/2008 | Angelides |

FOREIGN PATENT DOCUMENTS

| | | |
|---|---|---|
| DE | 196 39 226 A1 | 3/1998 |
| DE | 19 715 031 A1 | 10/1998 |
| EP | 0 373 413 A1 | 6/1990 |
| EP | 0 455 508 A1 | 11/1991 |
| EP | 0 732 590 A2 | 9/1996 |
| EP | 0 738 666 A2 | 10/1996 |
| EP | 0 811 843 A2 | 12/1997 |
| EP | 0 877 250 A2 | 11/1998 |
| EP | 0 909 952 A2 | 4/1999 |
| EP | 1 321 769 A1 | 6/2003 |
| EP | 1 329 395 A1 | 7/2003 |
| EP | 1 480 037 A1 | 11/2004 |
| EP | 1 855 110 A2 | 11/2007 |
| EP | 1 950 562 A2 | 7/2008 |
| WO | WO 92/17778 A1 | 10/1992 |
| WO | WO 94/10558 A1 | 5/1994 |
| WO | WO 94/19685 A1 | 9/1994 |
| WO | WO 97/48979 A1 | 12/1997 |
| WO | WO 98/19159 A1 | 5/1998 |
| WO | WO 99/13100 A1 | 3/1999 |

OTHER PUBLICATIONS

DE 19 639 226 A1 English Abstract.
DE 2 652 370 Machine Translation.

* cited by examiner

CONTAINER FOR DISPENSING A SINGLE TEST STRIP

BACKGROUND

Most persons that test their blood glucose level must do so several times per day. Therefore, for convenience, biosensors are typically packaged together for multiple tests by a user. Often, persons who must test their blood glucose level are afflicted with reduced or poor eyesight and/or limited hand dexterity. These conditions make it more difficult for these persons to see and grasp a single test strip or biosensor from a stack of many test strips. There are many types of test strip containers that store multiple test strips and dispense the test strips one at a time.

Various types of test strip containers store a stack of test strips in a housing and manually dispense a single test strip from the stack. One test strip container includes an engagement mechanism that frictionally engages a top surface of a test strip by applying a vertical force and a horizontal force to the topmost test strip to move a single test strip in a horizontal direction relative to the housing to dispense the single test strip. One problem with this type of engagement mechanism is the engagement mechanism must apply a sufficient vertical force and a sufficient horizontal force to the test strip in order to move the test strip. If a sufficient force in either direction is not applied then a test strip is not dispensed. If too much of a force in either direction is applied then it is possible that multiple test strips will be dispensed thereby creating waste.

Another type of test strip container includes a pusher head that projects by more than the thickness of a test strip. The projected portion of the pusher head engages a rear edge of a single test strip to push the single test strip out an opening of the test strip container. Accordingly, the pusher head must be manufactured to very specific dimensions and tolerances. One problem is the components of the container must be assembled to a very tight tolerance such that the projection of the pusher head is very close to or the same as the width of the single test strip. If either the assembly of the components or manufacture of the pusher head is not correct or within specified tolerances then this results in misalignment of the components of the test strip container and correspondingly malfunction of the test strip container.

Thus, there is a need for improvement in this field.

SUMMARY

Beneficially the test strip containers disclosed herein peel a single test strip from a stack of test strips stored therein by moving an outer member having a recessed slot about an inner member. The recessed slot is sized to receive and retain the single test strip as the outer member moves about the inner member. The recessed slot is also configured to allow the single test strip to slide within the slot. The inner member includes an internal storage compartment for the stack of test strips and an opening in the inner member allows passage of a test strip through the opening to the recessed slot in the outer member. The inner member includes an upwardly disposed ramp or track upon which a bottom-most edge of the single test strip rests against and rides along. Concurrently, the single test strip slides up the recessed slot as it travels along the ramp or track. No frictional engagement of the test strip is required to dispense a single test strip from the stack of test strips. Moreover, the outer member has a simple slot sized about equal to a single test strip. There is no complicated assembly of the outer member to the inner member; instead, the outer member is either attached to the exterior of the inner member or the outer member receives the whole inner member within it in a nesting relationship.

One test strip container described herein dispenses a single test strip from a stack of test strips stored in a container. A stack of test strips is stored in a test strip container with a mechanism that pushes the stack of test strips toward a test strip opening. Ease of test strip removal from the test strip container is achieved by moving a slider across an external face of the container such that a single test strip positioned in the test strip opening is captured in a recessed slot in the slider and peeled off the stack of test strips. The external face of the container includes a ramp or track in which an edge of the single test strip in the recessed slot of the slider rides along as the slider moves across the container towards a finger notch. The ramp or track extends from the test strip opening toward the notch to elevate the single test strip above an edge of the container. In a final dispensing position, the finger notch and the slider form a test strip dispensing opening from which the single test strip is dispensed such that a portion of the single test strip extends above the container for easy removal by a user.

Another test strip container described herein dispenses a single test strip or biosensor from a stack of test strips stored in an inner cylinder. The stack of test strips is stored in a test strip container with a mechanism that pushes the stack of test strips toward a test strip opening in the inner cylinder. Ease of test strip removal from the test strip container is realized by rotation of an outer cylinder about the inner cylinder such that a single test strip in the test strip opening is captured in a recessed slot in the outer cylinder. As the outer cylinder and the single test strip continue to rotate about the inner cylinder, the single test strip held in the recessed slot rides along an external angled ramp or track positioned on the inner cylinder that forces a portion of the single test strip to extend above edges of the inner and the outer cylinders for easy grasping by a user. Continued rotation of the recessed slot in the outer cylinder past the test strip opening causes the outer cylinder to cover the test strip opening.

Some or all of the above-mentioned features may be present in the corresponding independent or dependent claims but should not be construed to be a limitation unless expressly recited in a particular claim. This summary is provided to introduce a selection of the concepts that are described in further detail in the detailed description and drawings contained herein. This summary is not intended to identify any primary or essential features of the claimed subject matter nor is it intended to be used as an aid in determining the scope of the appended claims. Each embodiment described herein is not intended to address every object described herein, and each embodiment does not include each feature described. Other forms, embodiments, objects, advantages, benefits, features, and aspects of the present invention will become apparent to one of skill in the art from the detailed description and drawings contained herein.

DESCRIPTION OF THE SELECTED EMBODIMENTS

Figure 1:
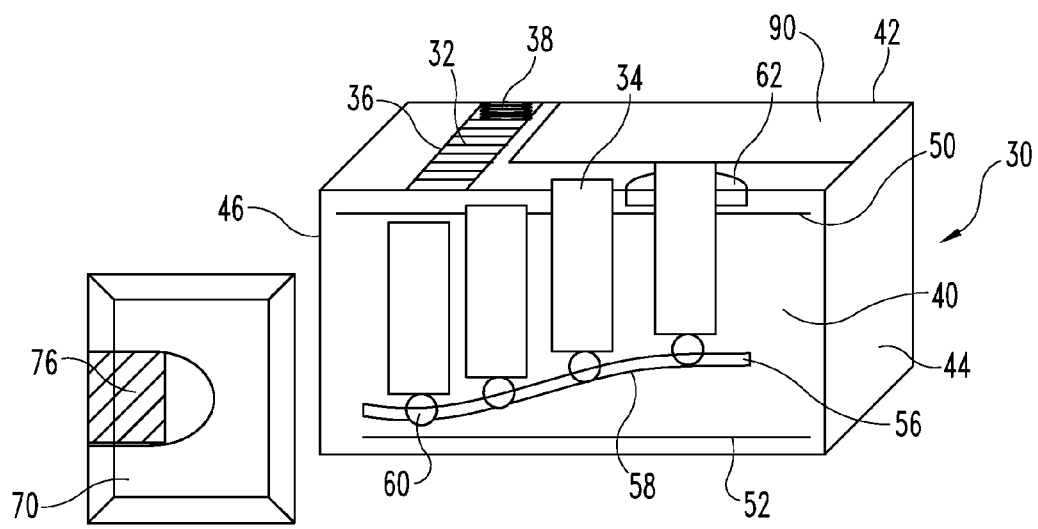
FIG. 1 is a top perspective view of a test strip container according to one embodiment wherein a single test strip is illustrated in an initial position, an intermediate position, a partially dispensed position, and a fully dispensed position.
Figure 2:
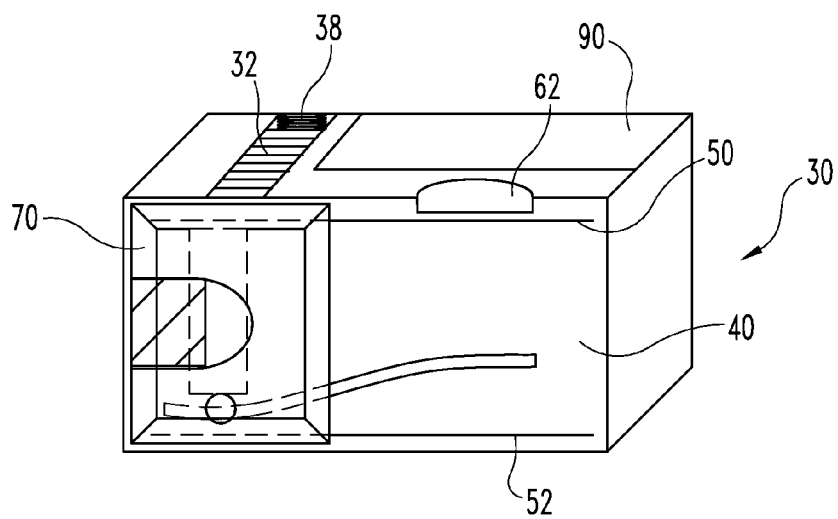
FIG. 2 is a top perspective view of a slider attached to the container from FIG. 1 wherein the single test strip is in an initial position.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. One embodiment of the invention is shown in great detail, although it will be apparent to those skilled in the relevant art that some features that are not relevant to the present invention may not be shown for the sake of clarity.

There has been a trend for persons to self monitor their blood glucose level or other health conditions by testing a body fluid sample, often multiple times per day, every day of the week. Typically, test strips are packaged and sold in a convenient stack stored in a test strip container. Those persons that must frequently test for various health conditions may have reduced eyesight and/or limited hand dexterity.

To address these issues, the test strip containers described herein uniquely and accurately dispense a single test strip from the stack such that a user simply has to slide a mechanism across the face of a test strip container or rotate an outer cylinder about an inner cylinder to elevate the single test strip above the remaining stack of test strips. A user can then see and easily grasp the single test strip for removal. As mentioned previously, no frictional engagement of the test strip is required to dispense a single test strip from the stack of test strips. Instead, a single test strip is peeled from the stack of test strips. Moreover, there is no complicated assembly of the components of the test strip container.

Figure 4:
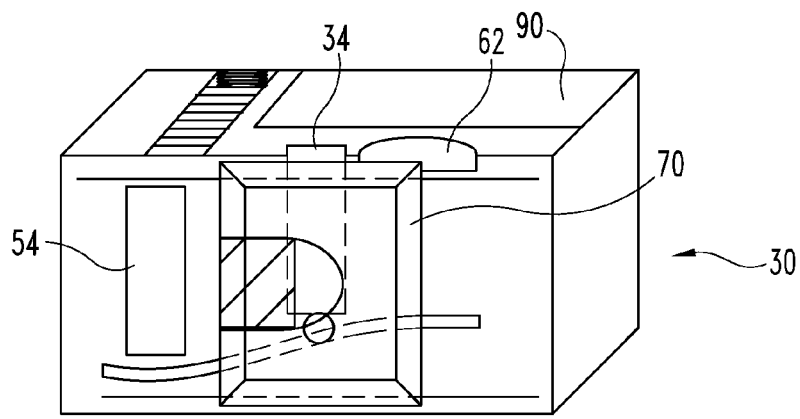
FIG. 4 is a top perspective view of the slider attached to the container from FIG. 1 wherein the single test strip is in a partially dispensed position.
Figure 5:
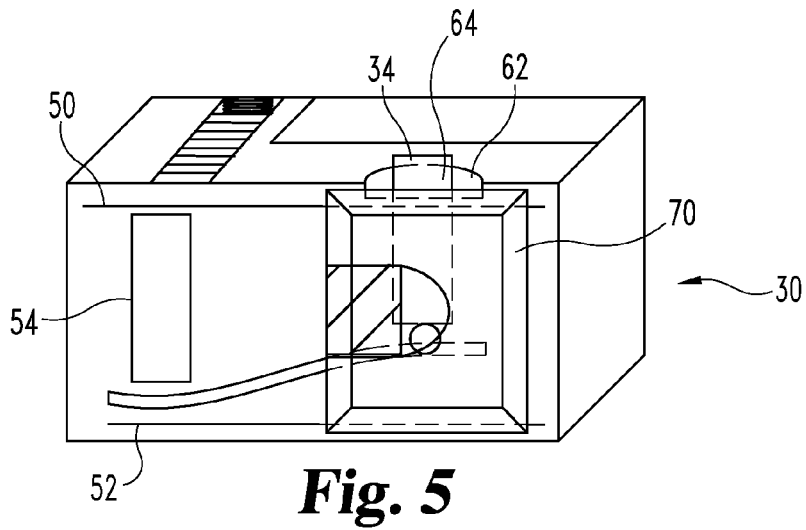
FIG. 5 is a top perspective view of the slider attached to the container from FIG. 1 wherein the single test strip is in a fully dispensed position.

A test strip container 30 according to one embodiment is described with reference to FIGS. 1, 2, 3, 4, 5, 6, and 7. The test strip container 30 is configured to store a stack of test strips 32, remove a single test strip 34 from the stack of test strips 32, and present the single test strip 34 for removal from the test strip container 30. The test strip container 30 includes a test strip compartment 36 for storing the stack of test strips 32 and a biasing mechanism 38 that biases or pushes the stack of test strips 32 towards a test strip opening 54 when the test strip compartment 36 and stack of test strips 32 are loaded into the test strip container 30. The test strip opening 54 of the test strip container 30 is aligned with the test strip compartment 36 such that the single test strip 34 passes through the test strip opening 54. In one form, one or more clips (not illustrated) are positioned in the test strip opening 54 to retain the remaining test strips after the single test strip 34 passes through the test strip opening 54. In one embodiment, a desiccant block (not illustrated) is positioned in the interior of the test strip container 30 in order to reduce the amount of moisture in the test strip container 30 and preserve the stack of test strips 32. The desiccant block can be formed from moldable material. In another form, a plastic material (not illustrated) is positioned in the test strip container 30 to maintain the test strip compartment 36 in alignment with the test strip opening 54 to dispense the stack of test strips 32 as shown in FIGS. 4 and 5.

In the illustrated embodiment, the test strip container 30 has a rectangular shape with a first wall 40 opposite a second wall 42 and a third wall 44 opposite a fourth wall 46. The first wall 40 includes a first rail 50 offset from a second rail 52 with the test strip opening 54 positioned between the first rail 50 and the second rail 52. The first rail 50 and the second rail 52 span across the first wall 40 and are positioned to retain a slider 70 as described below. The test strip opening 54 is sized to receive the single test strip 34 and allow the single test strip 34 to pass through.

The first wall 40 also includes a track 56 that is positioned between the first rail 50 and the second rail 52. The track 56 defines a groove 58 and a recessed pin 60 that floats up and down within the groove 58. In another embodiment, the track 56 could be a ramp. The groove 58 starts underneath the test strip opening 54, and the groove 58 stretches from the test strip opening 54 towards a notch 62 in the first wall 40. In the illustrated embodiment, the groove 58 has an elongated S-shape, and the pin 60 is circular in shape. Generally, when viewing FIGS. 1, 2, 3, 4, and 5, the groove 58 extends in an upward direction from the test strip opening 54 to the notch 62. The notch 62 and the slider 70 together define a test strip dispensing opening 64 from which the single test strip 34 from the test strip container 30 is dispensed, as described in more detail below.

Figure 6:
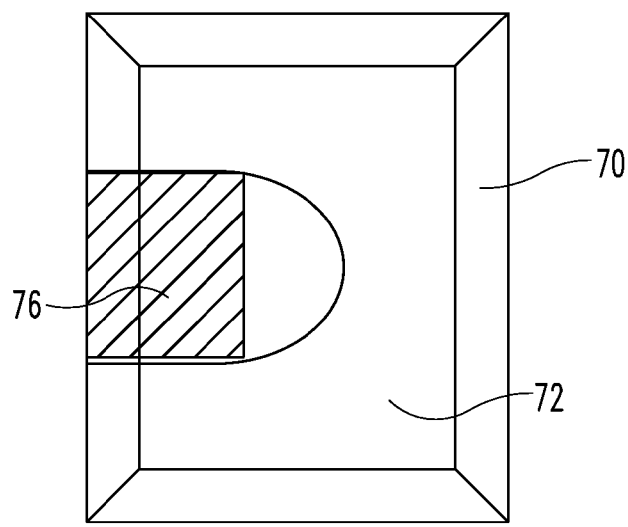
FIG. 6 is a front view of a slider.
Figure 7:
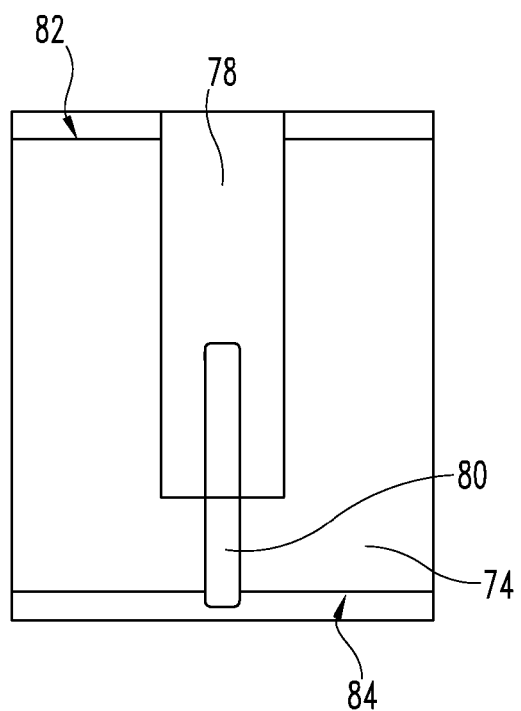
FIG. 7 is a rear view of the slider from FIG. 6.

The test strip container 30 also includes the slider 70 illustrated in FIGS. 6 and 7. The slider 70 and the track 56 work together to dispense the single test strip 34 as described in more detail below. The slider 70 has a front face 72 and an opposite rear face 74. In one form, the front face 72 has a finger grip 76 sized to receive a user's finger to assist a user in moving the slider 70 across the test strip container 30. The rear face 74 defines a recessed test strip slot 78 sized to receive and retain the single test strip 34 from the test strip opening 54. As the slider 70 travels across the test strip container 30 from the test strip opening 54 towards the notch 62, the single test strip 34 is retained in the test strip slot 78. The recessed test strip slot 78 has a depth and a width approximately equal to that of the single test strip 34. The rear face 74 defines a pin slot 80 sized to slidingly retain the pin 60 as the slider 70 travels across the test strip container 30. The pin slot 80 allows the pin 60 to float up and down with the direction of the groove 58. In other words, the recessed pin 60 rides partially in the pin slot 80 and partially in the groove 58 while the single test strip 34 rests on the recessed pin 60, and the single test strip 34 is retained in the test strip slot 78. The rear face 74 has a first lip 82 positioned opposite a second lip 84 such that the first lip 82 engages the first rail 50 and the second lip 84 engages the second rail 52 to retain the slider 70 on the test strip container 30 as the slider 70 travels across the test strip container 30. As the slider 70 travels over the notch 62, the slider 70 and notch 62 form the test strip dispensing opening 64 from which the single test strip 34 exits the test strip container 30 as illustrated in FIG. 5.

In the illustrated embodiment, the test strip container 30 also defines a waste compartment 90 for used test strips. In another embodiment, the test strip container 30 includes a meter.

Next, FIGS. 2, 3, 4, and 5 will be discussed with respect to dispensing the single test strip 34. In an initial position illustrated in FIG. 2, the slider 70 is positioned over the test strip opening 54. In this configuration, the slider 70 forms a seal with the test strip opening 54. The biasing mechanism 38 biases the stack of test strips 32 towards the test strip opening 54. As such, the single test strip 34 is received and retained in the recessed test strip slot 78 of the slider 70, and the single test strip 34 rests on the recessed pin 60 of track 56.

Figure 3:
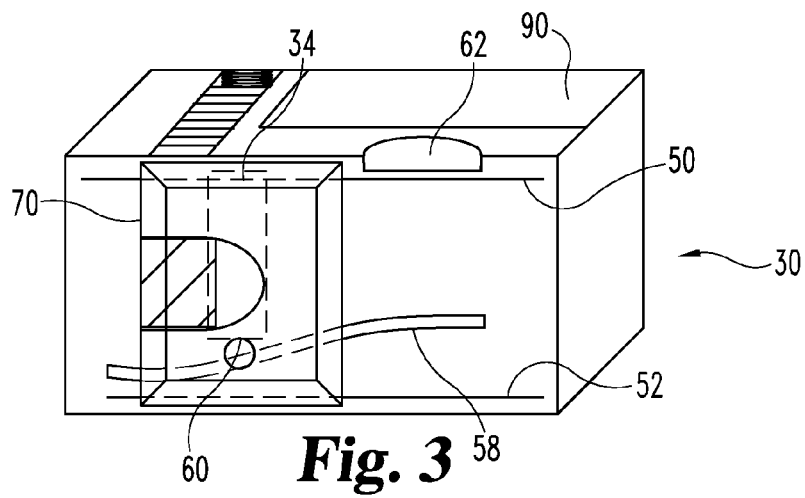
FIG. 3 is a top perspective view of the slider attached to the container from FIG. 1 wherein the single test strip is in an intermediate position.

To dispense the single test strip 34, a user or other mechanism engages the front face 72 or the finger grip 76 of the slider 70 and pushes the slider 70 across the test strip container 30 towards the notch 62 as shown in FIG. 3. The pin 60 rides along the groove 58 and the pin slot 80 which together force the pin 60 to move towards the notch 62. As the pin 60 travels along the groove 58 and the pin slot 80 with the single test strip 34 resting thereon, a portion of the single test strip 34 extends out of the test strip container 30 as shown in FIG. 4. As the slider 70 continues to move towards a fully dispensed position, the pin 60 continues to travel along both the groove 58 and the pin slot 80 towards the notch 62, and an additional portion of the single test strip 34 correspondingly continues to extend from the test strip container 30.

As the slider 70 passes over the notch 62, the single test strip 34 resting on the pin 60 extends through the test strip dispensing opening 64 formed by the recessed test strip slot 78 and the notch 62 as shown in FIG. 5. In this fully dispensed position, a portion of the single test strip 34 is positioned above an edge of the test strip container 30 for a user or mechanism to grasp and remove from the test strip container 30.

In the illustrated embodiment, the test strip container 30 is rectangular in shape; however, other container shapes, such as circular, can be utilized to dispense a single test strip as described below.

The following embodiments dispense a single test strip from a stack of test strips by rotating an outer cylinder about an inner cylinder to peel the single test strip from the stack and move the single test strip along a ramp to a dispensing position. The following embodiments describe two variations of an inner cylinder and two variations of an outer cylinder to dispense a single test strip from a stack.

Figure 8:
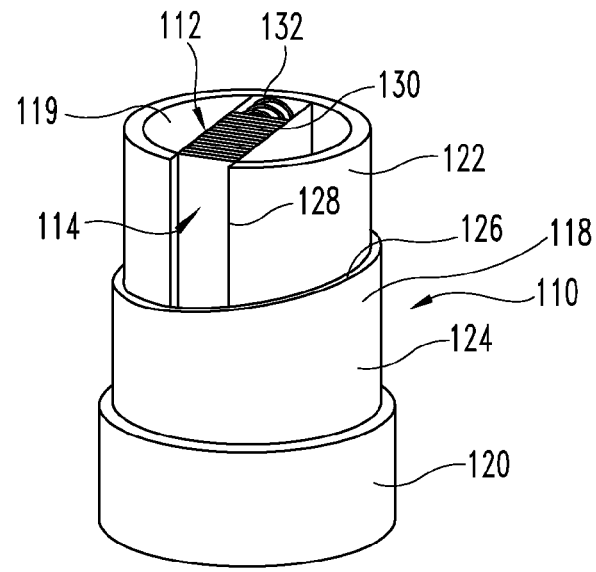
FIG. 8 is a top perspective view of an inner cylinder with a ramp for dispensing a single test strip according to one embodiment.

An inner cylinder 110 for dispensing a single test strip according to one embodiment is described with reference to FIG. 8. The inner cylinder 110 is configured to store a stack of test strips 112, remove a single test strip 114 from the stack of test strips 112, and present the single test strip 114 for removal from the inner cylinder 110 when the inner cylinder 110 is assembled with an outer cylinder 116 as described in more detail below. The inner cylinder 110 includes a hollow frame 118 mounted to a base 120. The hollow frame 118 defines an interior cavity 119 configured to store the stack of test strips 112. In one form, a desiccant material is stored in the interior cavity 119 around the stack of test strips 112, and the desiccant material is anchored to the base 120 or the hollow frame 118 to prevent the stack of test strips 112 from rotating. In another form, a test strip compartment 130 for storing the stack of test strips 112 is positioned in the interior cavity 119, and the test strip compartment 130 is anchored to the base 120 or the hollow frame 118 to prevent the stack of test strips 112 from rotating. A biasing mechanism 132 is located in the test strip compartment 130 such that the biasing mechanism 132 pushes the stack of test strips 112 towards a test strip opening 128 in the hollow frame 118.

The hollow frame 118 has a top portion 122 adjacent a bottom portion 124. Along an edge of the bottom portion 124 is a test strip ramp 126. In the illustrated embodiment, the test strip ramp 126 forms an intersection between the top portion 122 and the bottom portion 124. The top portion 122 defines the test strip opening 128 that is sized to receive the single test strip 114 from the stack of test strips 112 and allow the single test strip 114 to pass through the test strip opening 128 such that a bottom edge of the single test strip 114 rests on the test strip ramp 126. The test strip ramp 126 is positioned below the test strip opening 128, and the test strip ramp 126 is oriented diagonally relative to the hollow frame 118. To dispense the single test strip 114, an edge of the single test strip 114 travels along the test strip ramp 126 until an opposite end portion of the single test strip 114 extends above the top portion 122 as the outer cylinder 116 rotates about the inner cylinder 110 as described in more detail below. The outer cylinder 116 rests upon the base 120 when the outer cylinder 116 is assembled with the inner cylinder 110.

An inner cylinder 210 for dispensing a single test strip according to another embodiment is described with reference to FIG. 9. Inner cylinder 210 is similar to inner cylinder 110. The inner cylinder 210 is configured to store a stack of test strips 212, remove a single test strip 214 from the stack of test strips 212, and present the single test strip 214 for removal from the inner cylinder 210 when the inner cylinder 210 is assembled with an outer cylinder 116. The inner cylinder 210 includes a hollow frame 218 mounted to a base 220. The hollow frame 218 defines an interior cavity 219 configured to store the stack of test strips 212. In one form, a desiccant material is stored in the interior cavity 219 around the stack of test strips 212 and the desiccant material is anchored to the base 220 to prevent the stack of test strips 212 from rotating. In another form, a test strip compartment 230 for storing the stack of test strips 212 is positioned in the interior cavity 219 and the test strip compartment 230 is anchored to the base 220 to prevent the test strip compartment 230 from rotating. A biasing mechanism 232 is located in the test strip compartment 230 such that the biasing mechanism 232 pushes the stack of test strips 212 towards a test strip opening 228 in the hollow frame 218.

Figure 9:
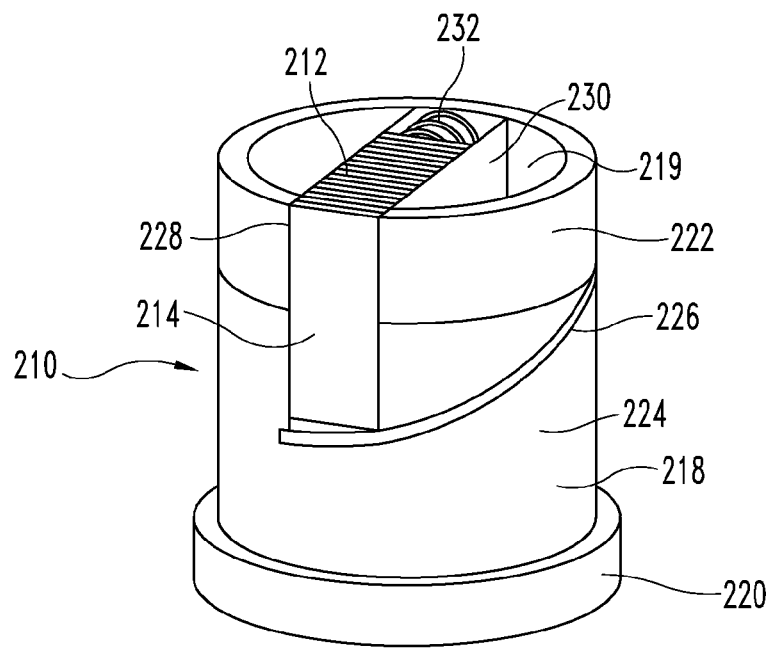
FIG. 9 is a top perspective view of an inner cylinder with a track for dispensing a single test strip according to another embodiment.

As shown in FIG. 9, the hollow frame 218 has a dispensing band 222 adjacent a bottom portion 224. The bottom portion 224 defines a test strip track 226 that extends from underneath the test strip opening 228 to the dispensing band 222 in a diagonal direction relative to the hollow frame 218. The test strip track 226 stops at the dispensing band 222 such that the single test strip 214 no longer moves once it reaches the dispensing band 222. The dispensing band 222 is configured such that an adequate portion of the single test strip 214 will extend above the dispensing band 222 for a user to grasp when the single test strip 214 is in a final dispensed position. The hollow frame 218 defines the test strip opening 228 that is sized to receive the single test strip 214 from the stack of test strips 212 and allow the single test strip 214 to pass through the test strip opening 228 such that a bottom edge of the single test strip 214 rests on the test strip track 226.

Figure 12:
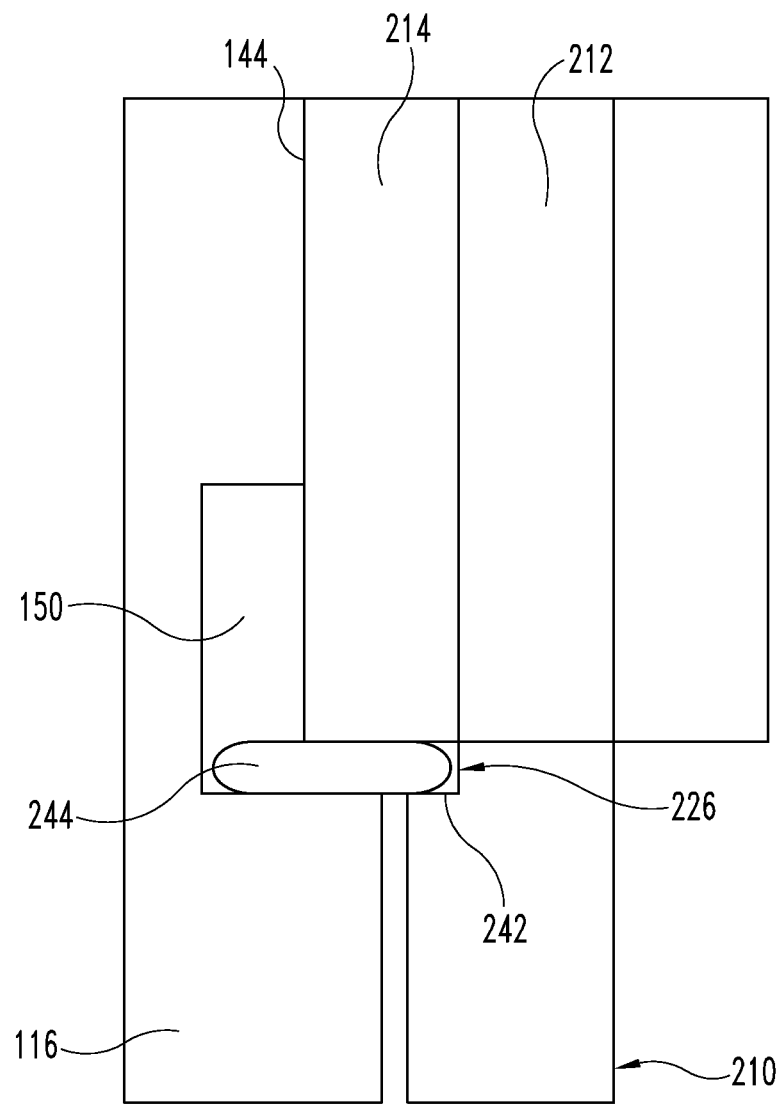
FIG. 12 is a cross sectional view of the embodiment illustrated in FIG. 11.

The test strip track 226 defines a groove 242 and a recessed pin 244 (illustrated in FIG. 12) that glides along groove 242. In the illustrated embodiment, the pin 244 has a substantially flat disc shape. In this embodiment or variation, the outer cylinder 116 defines a pin slot 150 that aligns with the groove 242 when the outer cylinder 116 is assembled with the inner cylinder 210. Together, the pin slot 150 and the groove 242 are sized to retain the recessed pin 244. An edge of the single test strip 214 rests on the pin 244. In an initial pre-dispensing position, the groove 242 is aligned at the bottom of the pin slot 150 when the outer cylinder 116 is assembled with the inner cylinder 210. While the outer cylinder 116 rotates about the inner cylinder 210, the pin 244 rides along the groove 242 and up the pin slot 150. The single test strip 214 rests on the pin 244 while the pin 244 travels along the groove 242 and floats to the top of the pin slot 150 to cause an opposite end portion of the single test strip 214 to extend above the dispensing band 222 as the outer cylinder 116 rotates about the inner cylinder 210. In a final dispensing position, pin 244 reaches the top of the pin slot 150 and the end of the groove 242 by the dispensing band 222.

Figure 10:
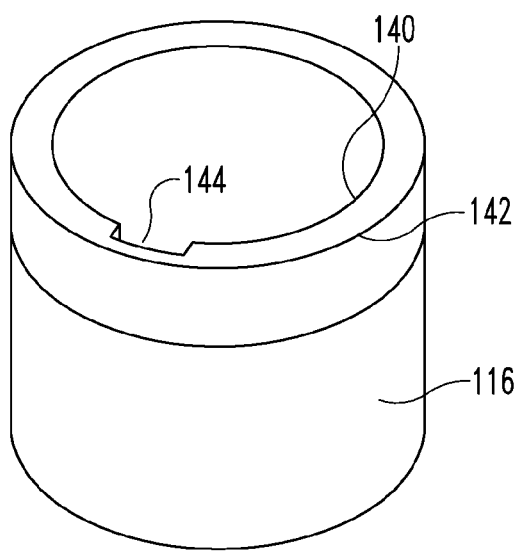
FIG. 10 is a top perspective view of an outer cylinder that assembles with either the FIG. 8 or FIG. 9 embodiment for dispensing a single test strip.
Figure 11:
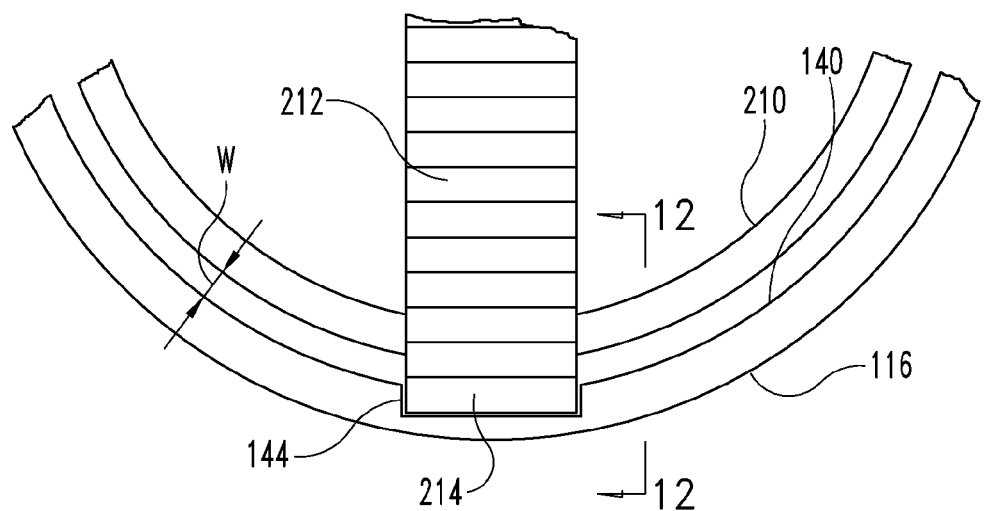
FIG. 11 is a partial top view of the inner cylinder from FIG. 8 or FIG. 9 assembled with the outer cylinder from the FIG. 10 embodiment.

The outer cylinder 116, illustrated in FIG. 10, includes an inner wall 140 and an outer wall 142. The outer cylinder 116 is sized to receive the inner cylinder 110 and mount to the base 120. Similarly, the outer cylinder 116 is sized to receive the inner cylinder 210 and mount on the base 220. The inner wall 140 defines a recessed test strip slot 144 sized to receive and retain the single test strip 114 as the outer cylinder 116 rotates about either the inner cylinder 110 or the inner cylinder 210 as shown in FIG. 11. The depth of the recessed test strip slot 144 is slightly less than the thickness of the single test strip 214. In one form or variation, illustrated in FIG. 12, the outer cylinder 116 defines the pin slot 150 adjacent the recessed test strip slot 144. The embodiment illustrated in FIG. 12 for the outer cylinder 116 with the pin slot 150 is used with the inner cylinder 210. The outer cylinder 116 used with inner cylinder 110 may not require the pin slot 150; however, the pin slot 150 may be included. In one form, the outer cylinder 116 includes a finger grip to aid in handling and rotating the outer cylinder 116 about the inner cylinder 110 or 210.

One example of a depth of the recessed test strip slot 144 is approximately 0.3 to 0.4 millimeters. One example of a gap width, W, illustrated in FIG. 11, between the inner cylinder 110 and the outer cylinder 116 is 0.4 to 0.5 millimeters. The total sum of the depth of the recessed test strip slot 144 and the gap width is less than the sum of the thickness of two of the single test strips 214. In one form, the single test strip 214 has a thickness of about 0.55 millimeters.

The language used in the claims and specification is to only have its plain and ordinary meaning, except as explicitly defined above. The words in the above definitions are to only have their plain and ordinary meaning. Such plain and ordinary meaning is inclusive of all consistent dictionary definitions from the most recently published Webster's dictionaries and Random House dictionaries.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An apparatus for dispensing test strips, comprising:
   a container configured to store a stack of the test strips, the container defining a test strip opening sized to allow passage of the stack of test strips, the container having an external track;
   an external member positioned over the external track on the container, the external member configured to retain a single test strip from the stack of test strips; and
   the external member configured to travel over the container to dispense the single test strip, wherein an edge of the single test strip rides on the external track and the single test strip moves across an external surface of the container.

2. The apparatus of claim 1, wherein the external member includes a front face and an opposite rear face, wherein the rear face defines a slot recessed opening therein that is sized to retain the single test strip from the stack of test strips.

3. The apparatus of claim 1, wherein the external member is a slider.

4. The apparatus of claim 3, wherein the container further includes a top rail and a bottom rail; and
   the slider includes a first lip and a second lip, the first lip positioned on the slider to engage the top rail and the second lip positioned on the slider to engage the bottom rail when the slider is assembled with the container.

5. The apparatus of claim 3, wherein the container includes a notch, and the slider and the notch define a test strip dispensing opening when the slider is in a fully dispensed position, the test strip dispensing opening configured to dispense the single test strip.

6. The apparatus of claim 3, further comprising:
   wherein the external track defines a groove;
   the slider defines a pin slot; and
   a pin is configured to ride in the groove and the pin slot, wherein the single test strip rests on the pin.

7. The apparatus of claim 1, wherein the track includes an angled ramp, and the single test strip directly rides along the angled ramp for dispensing the test strips one at a time.

8. The apparatus of claim 1, wherein the external member is an outer cylinder and the container is an inner cylinder, the outer cylinder being rotatable about the inner cylinder.

9. A method of dispensing test strips, comprising:
   positioning a stack of the test strips in a container;
   moving an external member along an exterior surface of the container to capture a single test strip from the stack of test strips in a recessed slot opening defined in the external member, wherein the exterior surface includes an exterior ramp; and
   moving the captured single test strip in a transverse direction along the exterior surface of the container while an edge of the captured single test strip rides on the exterior ramp to dispense the single test strip.

10. The method of claim 9, further comprising:
    wherein the container is an inner cylinder and the external member is an outer cylinder;
    nesting the inner cylinder in the outer cylinder; and
    rotating the outer cylinder about the inner cylinder to dispense the single test strip.

* * * * *